United States Patent
Kawata

(10) Patent No.: US 8,859,757 B2
(45) Date of Patent: Oct. 14, 2014

(54) SEPARATING AGENT FOR OPTICAL ISOMERS

(75) Inventor: Yuki Kawata, Himeji (JP)

(73) Assignee: Daicel Corporation, Osaka-shi, Osaka (JP)

( * ) Notice: Subject to any disclaimer, the term of this patent is extended or adjusted under 35 U.S.C. 154(b) by 5 days.

(21) Appl. No.: 13/702,203

(22) PCT Filed: Jun. 17, 2011

(86) PCT No.: PCT/JP2011/063914
§ 371 (c)(1),
(2), (4) Date: Dec. 5, 2012

(87) PCT Pub. No.: WO2011/158935
PCT Pub. Date: Dec. 22, 2011

(65) Prior Publication Data
US 2013/0079507 A1    Mar. 28, 2013

(30) Foreign Application Priority Data

Jun. 18, 2010    (JP) ................................. 2010-139485

(51) Int. Cl.
| | | |
|---|---|---|
| *C07H 1/00* | (2006.01) | |
| *C08B 33/00* | (2006.01) | |
| *C07B 57/00* | (2006.01) | |
| *B01J 20/286* | (2006.01) | |
| *B01J 20/29* | (2006.01) | |
| *G01N 30/88* | (2006.01) | |

(52) U.S. Cl.
CPC ........ *C08B 33/00* (2013.01); *G01N 2030/8877* (2013.01); *C07B 57/00* (2013.01); *B01J 20/286* (2013.01); *B01J 20/29* (2013.01)
USPC .......................................................... 536/54

(58) Field of Classification Search
CPC ................................ C08B 15/06; C08B 33/00
See application file for complete search history.

(56) References Cited

U.S. PATENT DOCUMENTS

| | | | |
|---|---|---|---|
| 5,202,433 A * | 4/1993 | Okamoto et al. | ............. 540/200 |
| 5,491,223 A | 2/1996 | Okamoto | |
| 5,663,311 A | 9/1997 | Okamoto | |
| 2007/0039890 A1 * | 2/2007 | Okamoto et al. | ............. 210/656 |

FOREIGN PATENT DOCUMENTS

| | | |
|---|---|---|
| JP | 61-176538 | 8/1986 |
| JP | 62-21152 | 9/1987 |
| JP | 01-290635 A | 11/1989 |
| JP | 05-239103 | 9/1993 |
| JP | 06-211902 | 8/1994 |
| JP | 3148032 | 1/2001 |
| JP | 2001-124752 | 5/2001 |
| JP | 2005-017174 | 1/2005 |
| WO | WO 92/15616 | 9/1992 |

OTHER PUBLICATIONS

Dimethyl-, dichloro- and chloromethylphenylcarbamates of amylose as chiral stationary phases for high-performance liquid chromatography, by Bezhan Chankvetadze et al, Journal of Chromatography A, 694 (1995) pp. 101-109.
International Search Report Form PCT/ISA/210 mailed Aug. 16, 2011 (2 pages).
First Office Action of China Patent Office issued in China Patent Application No. 201180030061.7 with English translation dated Dec. 13, 2013 (18 pages).

* cited by examiner

*Primary Examiner* — Elli Peselev
(74) *Attorney, Agent, or Firm* — Flynn, Thiel, Boutell & Tanis, P.C.

(57) ABSTRACT

A separating agent for optical isomers that uses a polysaccharide derivative provided by replacing all or a portion of the hydrogen atoms on the hydroxyl groups present in a polysaccharide with two specific atomic groups that act on optical isomers targeted for separation in an optical resolution, wherein the sum of the average introduction ratios of specific terminal substituents in these atomic groups is greater than 3.0 per monosaccharide unit.

5 Claims, 1 Drawing Sheet

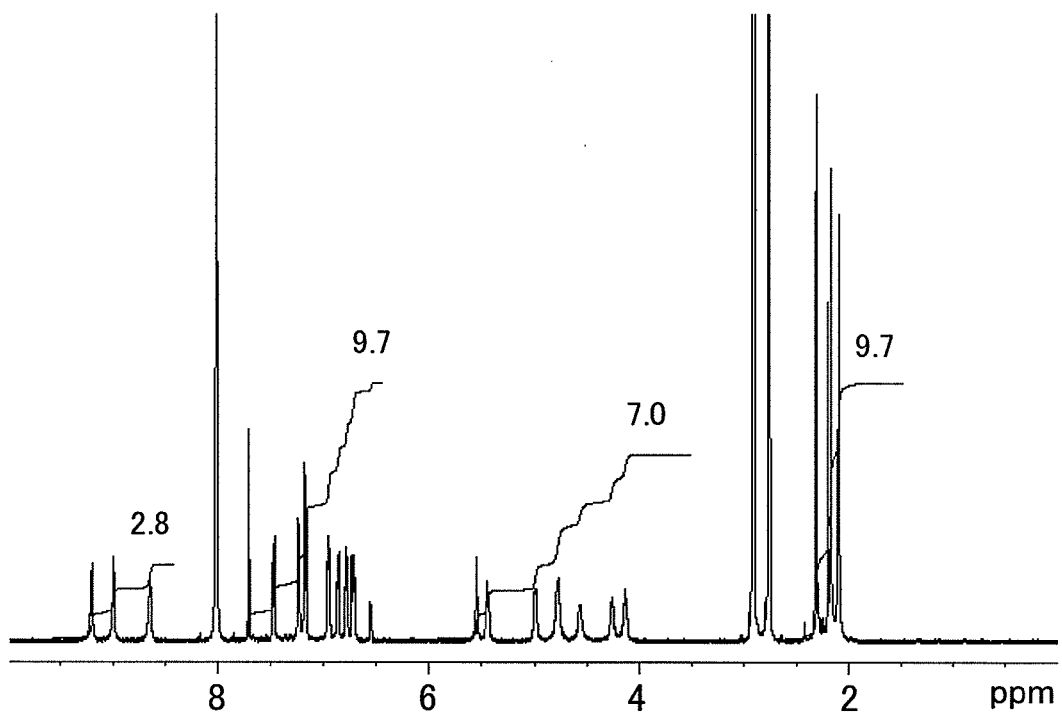

SEPARATING AGENT FOR OPTICAL ISOMERS

BACKGROUND OF THE INVENTION

Field of the Invention

The present invention relates to a separating agent for optical isomers.

The physical and chemical properties of optical isomers are entirely the same, but in some cases differences are seen in their functions to a biological body. As a consequence, the production of compounds that exhibit a high optical purity is an extremely important problem in fields such as medicines and pharmaceuticals. Fractionation methods based on high-performance liquid chromatography using separating agents for optical isomers are known to be techniques that respond to this problem.

Among the numerous separating agents for optical isomers, an enantioselective recognition ability for a broad range of compounds is known to be exercised in particular by separating agents in which a carbamate or ester derivative of a cellulose or amylose is supported on a silica gel.

Investigations are underway to improve the chromatographic fractionation productivity of chromatographic fractionation methods, and there is desire for a separating agent for optical isomers that provides an even better separation of the compounds to be fractionated, i.e., that has an even higher separation factor (α value).

For example, the phenylcarbamate derivatives of amylose are known as separating agents for optical isomers (refer, for example, to J. Chromatogr. A 694 (1995) pp. 101-109, Japanese Patent Publication No. 3148032, and Japanese Patent Application Laid-open No. 2005-17174).

With regard to the optical resolving power of the phenylcarbamate derivatives of amylose, an optical resolving power is generally known for these derivatives in which the average introduction ratio for the phenylcarbamate group per furanose ring or pyranose ring in the amylose is less than or equal to 3.

Further features of the present invention will become apparent from the following description of exemplary embodiments (with reference to the attached drawings).

SUMMARY OF THE INVENTION

The present invention provides a separating agent for optical isomers that contains a cellulose derivative or amylose derivative that has an excellent enantioselective recognition ability.

During their investigations into cellulose derivative-based and amylose derivative-based separating agents for optical isomers, the present inventors discovered that in some instances a different optical resolving power was exhibited between derivatives into which the same substituent had been introduced. The present invention was achieved as a result of intensive investigations directed to explaining this phenomenon.

Thus, the present invention provides a separating agent for optical isomers that contains a polysaccharide derivative, wherein this polysaccharide derivative is provided by replacing all or a portion of hydrogen atoms on hydroxyl groups present in a cellulose or an amylose with the atomic groups represented by Formulae (1) and (2) below, and a sum of the average introduction ratios per monosaccharide unit of R1 and R2 in Formulae (1) and (2) below is greater than 3.0.
C 1

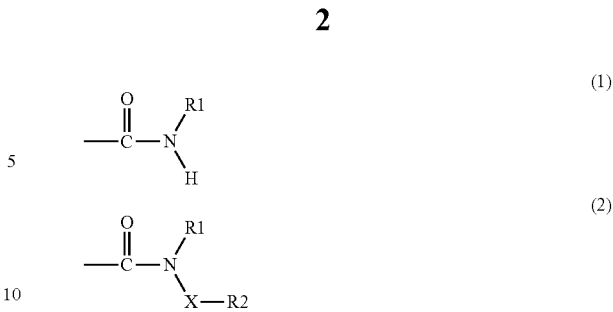

In the preceding formulas, R1 and R2 each represent a $C_{1-18}$ monovalent aliphatic group which may have substituent or a $C_{6-18}$ monovalent aromatic group which may have substituent and X represents a single bond or a divalent organic group.

The present invention also provides the aforementioned separating agent for optical isomers, in which the X represents an amide bond.

The present invention further provides the aforementioned separating agent for optical isomers, in which the R1 and R2 are the same.

The present invention, because it uses a cellulose derivative or amylose derivative in which the average introduction ratio of the substituents in the cellulose derivative or amylose derivative exceeds 3.0, can provide a separating agent for optical isomers that contains a cellulose derivative or amylose derivative that has an excellent enantioselective recognition ability.

BRIEF DESCRIPTION OF THE DRAWINGS

FIG. 1 is a chart that gives the $^1$N-NMR spectrum of the amylose derivative 1 obtained in Example 1.

DESCRIPTION OF THE EMBODIMENTS

The separating agent for optical isomers of the present invention contains a polysaccharide derivative. In the present invention, this polysaccharide derivative is provided by replacing all or a portion of the hydrogen atoms on the hydroxyl groups present in cellulose or amylose with the atomic groups represented by the Formulae (1) and (2) given below. Thus, all of the hydrogen atoms on the hydroxyl groups may be substituted by these atomic groups in this polysaccharide derivative or a portion of the hydrogen atoms on these hydroxyl groups may be substituted by these atomic groups.
C 2

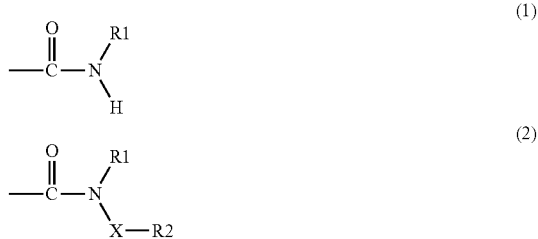

In terms of higher order structure formation by the polysaccharide derivative, the number-average degree of polymerization (average number of pyranose rings or furanose rings (monosaccharide units) present in 1 molecule of the cellulose or amylose) of the cellulose or amylose in this polysaccharide derivative is preferably at least 5 and more preferably is at least 10. While there is no particular upper limit on the number-average degree of polymerization of this polysaccharide, its number-average degree of polymerization is preferably not more than 1,000 in terms of ease of handling. Given these considerations, this polysaccharide has a number-average degree of polymerization preferably of from 5 to 1,000, more preferably 10 to 1,000, and even more preferably 10 to 500.

R1 and R2 each represent a $C_{1-18}$ monovalent aliphatic group which may have substituent or a $C_{6-18}$ monovalent aromatic group which may have substituent. R1 and R2 may be the same as each other or may differ from one another. The substituents that may be present on R1 and R2 can be exemplified by $C_{1-18}$ alkyl groups, halogen, amino groups, and $C_{1-18}$ alkoxyl groups. The alkyl group here may have a chain or a cyclic configuration. R1 and R2 can be exemplified by the methyl group, octadecyl group, phenyl group, naphthyl group, cyclohexyl group, norbornenyl group, 3-chloro-4-methylphenyl group, 3,5-dichlorophenyl group, 3,5-dimethylphenyl group, 5-chloro-2-methylphenyl group, 4-methylphenyl group, and 4-chlorophenyl group.

The aforementioned X represents a single bond or a divalent organic group. With regard to this X, "—X—R2" is preferably a functional group that acts in the optical resolution of the optical isomers targeted for separation in the optical resolution. This X can be exemplified by the amide bond, urethane bond, ether bond, ester bond, and divalent groups that contain these bonds.

The sum of the average introduction ratios for the R1 and R2 in the aforementioned polysaccharide derivative in the present invention is greater than 3.0 per monosaccharide unit. This sum of the average introduction ratios for R1 and R2 per monosaccharide unit is the sum of the average introduction ratio for R1 per monosaccharide unit and the average introduction ratio for R2 per monosaccharide unit. Viewed from the perspective of excessive changes in the higher order structure due to steric hindrance within the polysaccharide derivative, this average introduction ratio is preferably not more than 5.0 and more preferably is not more than 4.0. Viewed from the perspective of obtaining satisfactory effects through an increase in the average introduction ratio, this average introduction ratio is preferably at least 3.05 and more preferably is at least 3.1.

The average introduction ratio under consideration can be measured, for example, by NMR analysis. For example, with reference to the $^1$H-NMR spectrum of the polysaccharide derivative, this average introduction ratio can be determined from the peak area originating from the hydrogen atoms specific to R1 or R2 and the peak area originating from the hydrogen atoms specific to the polysaccharide skeleton.

The atomic group with Formula (1) can be introduced into cellulose or amylose by reacting the hydroxyl groups in the cellulose or amylose with an isocyanate derivative that corresponds to the atomic group with Formula (1). For example, a known method in which a carbamate bond is formed by reacting the hydroxyl group in the polysaccharide with the corresponding isocyanate derivative can be used as such a method of introducing Formula (1) (refer, for example, to Patent Document 1 and Non-Patent Document 1).

The reaction of a compound corresponding to "—X—R2" with the amino group in the cellulose derivative or amylose derivative bearing the atomic group with Formula (1) can be used to introduce the atomic group with Formula (2) into the cellulose derivative or amylose derivative. The method of introducing this atomic group with Formula (2) can be exemplified by a method in which an allophanate ester is produced by reacting the hydrogen atom in the amino group in Formula (1) with an isocyanate derivative corresponding to "—X—R2", and by an acylation method in which the hydrogen atom in the amino group in Formula (1) is reacted with an acid anhydride or acid chloride that corresponds to "—X—R2".

When X represents an amide bond, the isocyanate derivative corresponding to the atomic group with Formula (1) and the isocyanate derivative corresponding to "—X—R2" are then both isocyanate derivatives. As a consequence, in such cases the polysaccharide derivative in which X represents an amide bond can be obtained by reacting cellulose or amylose with the isocyanate derivative corresponding to Formula (1) followed by reaction with the isocyanate derivative corresponding to "—X—R2". Or, the polysaccharide derivative in which X represents an amide bond can be obtaining by carrying out carbamate bond formation and allophanate ester production at the same time by reacting both of the aforementioned isocyanate derivatives, at a greater excess as the total amount than in the aforementioned known method of carbamate bond formation, with the hydroxyl groups in the cellulose or amylose.

When X represents an amide bond and R1 is also the same as R2, the same isocyanate derivative can be used for the isocyanate derivative that corresponds to the Formula (1) atomic group and the isocyanate derivative that corresponds to "—X—R2". As a consequence, a polysaccharide derivative can be obtained in this case in which X represents an amide bond and R1 is the same as R2 by carrying out carbamate bond formation and allophanate ester production at the same time by reacting the corresponding isocyanate derivative, at a greater excess than in the aforementioned known method of carbamate bond formation, with the hydroxyl groups in the cellulose or amylose.

Taking into consideration the deactivation of the isocyanate by the moisture present in the system, the amount of the aforementioned isocyanate derivative used for the synthesis of the polysaccharide derivative under consideration, expressed with reference to the total hydroxyl group in the cellulose or amylose, is preferably at least 1.3 equivalents, more preferably at least 2.5 equivalents, and even more preferably at least 3.0 equivalents. While there are no particular limitations on the upper limit for the amount of isocyanate derivative used, not more than 10 equivalents is preferred from the standpoint of the plateauing out of the effects.

Considered from the perspective of carrying out carbamate bond formation and allophanate ester production at the same time, the reaction temperature in the synthesis of the aforementioned polysaccharide derivative is preferably lower than the usual temperatures in synthesis methods that form the carbamate bond under consideration or is on the low end of the usual temperature range. Based on this perspective, the reaction temperature is preferably from 60° C. to 110° C. and more preferably is 70° C. to 90° C.

The polysaccharide in this polysaccharide derivative is more preferably amylose from the standpoint of increasing the aforementioned average introduction ratio.

There are no particular limitations on the separating agent for optical isomers of the present invention as long as this separating agent takes a form that contains the hereinabove-described polysaccharide derivative. The separating agent for optical isomers of the present invention may comprise only this polysaccharide derivative, or the polysaccharide derivative may be supported on a carrier.

The separating agent for optical isomers comprising only the polysaccharide derivative may be prepared by molding the polysaccharide derivative into a cylindrical porous body held in a columnar tube. The separating agent for optical isomers comprising only the polysaccharide derivative may also be prepared by crushing or spheronizing the polysaccharide derivative itself. Viewed from the standpoint of increasing the separation degree, the particles of the separating agent for optical isomers are preferably particles that have been subjected to a spheronizing treatment, and the particles also preferably have an uniformized particle size. The separating agent for optical isomers can be crushed by known methods and can be subjected to a spheronizing treatment by known methods. The granulometry can be adjusted, for example, by classification and by the mixing of classified products.

The separating agent for optical isomers comprising the aforementioned polysaccharide derivative supported on a carrier can be prepared by supporting the polysaccharide derivative on a carrier. This carrier should be capable of supporting the polysaccharide derivative, but is not otherwise particularly limited. This carrier can be any of the various carriers known for use in the chromatography described above and can be exemplified by porous organic carriers and porous inorganic carriers with porous inorganic carriers being preferred. The porous organic carriers can be exemplified by polymers such as polystyrene, polyacrylamide, polyacrylate, and derivatives of the preceding. The porous inorganic carriers can be exemplified by silica gel, alumina, magnesia, glass, kaolin, titanium oxide, silicates, and hydroxyapatite, wherein silica gel is particularly preferred.

The carrier may be a cylindrical porous body held in a columnar tube or may be a particulate carrier. The particle size of the carrier is preferably from 0.1 µm to 10 mm, more preferably from 1 µm to 300 µm, and even more preferably from 1 µm to 75 µm. The average pore diameter of the porous carrier is preferably from 1 nm to 100 µm and more preferably from 5 nm to 5,000 nm. When the carrier is silica gel, the surface of the silica gel is desirably subjected to a surface treatment in order to extinguish the influence of residual silanol, but the surface treatment need not be carried out exhaustively. This surface treatment can be performed using a known method.

The method by which the polysaccharide derivative is supported on the carrier is not particularly limited. This regime can be exemplified by physical adsorption by the polysaccharide derivative to the carrier, chemical bonding between the carrier and the polysaccharide derivative, and chemical bonding of the polysaccharide derivative with itself on the carrier.

This physical adsorption can be carried out, for example, by a method in which the polysaccharide derivative is dissolved in a solubilizing solvent; for example, the carrier is immersed in the resulting solution in order to coat the carrier with the solution; and the solvent is removed from the carrier under reduced pressure, with the application of heat, or under a gas current. The chemical bonding can be exemplified by chemical bonding through the intermediary of a third component between the carrier and the polysaccharide derivative and by chemical bonding between the carrier and polysaccharide derivative brought about by exposure of the polysaccharide derivative adsorbed on the carrier to light or radiation and by the thereby induced radical reaction. Supporting the polysaccharide derivative on the carrier can be performed using known methods.

The amount of polysaccharide derivative supported on the carrier will vary with the method of separating the optical isomers and the type of carrier, but, expressed with reference to the carrier, is preferably 1 to 100 weight parts, more preferably 5 to 60 weight parts, and even more preferably 10 to 50 weight parts.

The separating agent for optical isomers of the present invention can be used in various applications for separating optical isomers by establishing an appropriate configuration in correspondence to the application for separating optical isomers. When, for example, the separating agent for optical isomers has a particulate configuration or a cylindrical porous body configuration, the separating agent for optical isomers can be used in methods that use it as packed in a column. Such methods can be exemplified by gas chromatography, liquid chromatography, supercritical fluid chromatography, and simulated moving bed chromatography. When the separating agent for optical isomers has a particulate configuration, it can be used in thin-layer chromatography.

The separating agent for optical isomers of the present invention can be used for membrane-based separations by supporting the polysaccharide derivative in a membrane. In addition, the separating agent for optical isomers of the present invention can be used in capillary columns by coating the polysaccharide derivative on the capillary column.

EXAMPLES

The method of the present invention is described herebelow by practical examples; however, the present invention is not limited by the scope of these examples.

Example 1

Synthesis of Amylose Derivative 1

An amylose derivative 1 was obtained by stirring the following in dry pyridine at 110° C. for 24 hours in a nitrogen atmosphere: amylose and 4 equivalents, with reference to the hydroxyl groups in the amylose, of 3-chloro-4-methylphenyl isocyanate. The resulting amylose derivative 1 was submitted to measurement by $^1$H-NMR using deuterated dimethylformamide as the solvent. The obtained $^1$H-NMR spectrum is shown in FIG. 1.

The average introduction ratio R for the 3-chloro-4-methylphenyl group per monosaccharide unit in the obtained amylose derivative 1, as calculated using Equation (1) below from the results of this $^1$H-NMR measurement, was 3.2. In Equation (1), A represents the peak area originating with the hydrogen in the methylene and methine of the amylose skeleton (δ=4.0 to 6.0 ppm); B represents the peak area originating with the hydrogen of the benzene ring (δ=6.5 to 7.8 ppm); and S represents the number of hydrogens in the benzene ring. A is 7.0 and B is 9.7 according to FIG. 1 and S is 3 according to the chemical structure of the amylose derivative 1.

$$R=7B/(S\times A) \qquad (1)$$

Preparation of a Separating Agent for Optical Isomers 1

5 g of the amylose derivative 1 obtained in the preceding synthesis example was dissolved in 30 mL tetrahydrofuran (THF); this THF solution was uniformly coated on 20 g of a silica gel that had a particle size of 5 µm; and the THF was distilled off to provide a separating agent for optical isomers 1 in which the amylose derivative 1 was supported on the silica gel.

Preparation of a Column 1 for Optical Isomer Separation

Using a slurry filling process, the separating agent for optical isomers 1 was filled into a stainless steel column that had an internal diameter of 0.46 cm x length of 25 cm, to provide a column 1 for optical isomer separation.

Evaluation

The column 1 for optical isomer separation was used to separate the enantiomers of the following by high-performance liquid chromatography: trans-stilbene oxide with Formula (ra-1) below, binaphthol with Formula (ra-2) below, Wieland-Miescher ketone with Formula (ra-3) below, benzoyloxy-2-azetidinone with Formula (ra-4) below, and fenoprofen with Formula (ra-5) below. The separation conditions for these optical resolutions were as follows: n-hexane/2-propanol=90/10 (volume ratio) was used for the eluent for (ra-1) and (ra-2); n-hexane/2-propanol=80/20 (volume ratio) was used for the eluent for (ra-3); acetonitrile was used for the eluent for (ra-4); acetonitrile/trifluoroacetic acid=100/0.1 (volume ratio) was used for the eluent for (ra-5); and the eluent flow rate was 1.0 mL/min in all instances. The resulting chromatograms were used to calculate the retention factor $k'_1$ for the more weakly adsorbed component (raffinate component), the retention factor $k'_2$ for the more strongly adsorbed component (the extract component), and the separation factor α. The retention factor $k'_1$ for the raffinate component was determined using Equation (2) below; the retention factor $k'_2$ for the extract component was determined using Equation (3) below; and the separation factor α was determined using Equation (4) below. In these equations, $t_0$ represents the dead time (elution time for tri-tert-butylbenzene); $t_1$ represents the elution time for the raffinate component; and $t_2$ represents the elution time for the extract component. The results of the optical resolutions are given in Table 1.

$$k'_1 = (t_1 - t_0)/t_0 \quad (2)$$

$$k'_2 = (t_2 - t_0)/t_0 \quad (3)$$

$$\alpha = k'_2/k'_1 \quad (4)$$

C 3

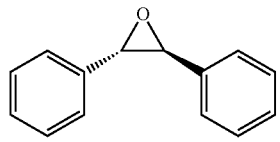
(ra-1)

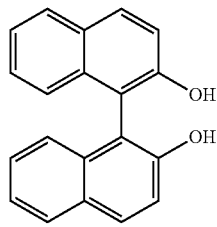
(ra-2)

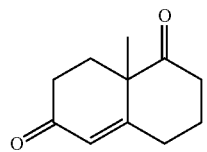
(ra-3)

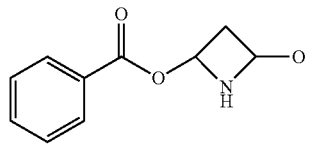
(ra-4)

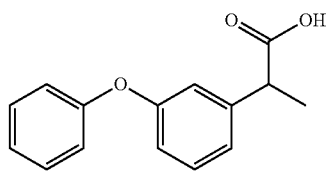
(ra-5)

TABLE 1

| racemic body | Example 1 | | Comparative Example 1 | |
|---|---|---|---|---|
| | $k'_1$ | α | $k'_1$ | α |
| trans-stilbene oxide | 0.82 | 1.45 | 0.72 | 1.38 |
| binaphthol | 3.19 | 1.20 | 3.46 | 1.06 |
| Wiland-Miescher ketone | 4.17 | 1.77 | 5.67 | 1.66 |
| benzoyloxy-2-azetidinone | 0.75 | 3.10 | 1.06 | 2.24 |
| fenoprofen | 0.13 | 1.33 | 0.08 | 1.00 |

Column 1 for optical isomer separation was also used to separate the enantiomers of the following by high-performance liquid chromatography: γ-phenyl-γ-butyrolactone with Formula (rac-6) below, tiaprofenic acid with Formula (rac-7) below, and diprophylline with Formula (rac-8) below. The separation conditions for these optical resolutions were as follows: n-hexane/2-propanol=80/20 (volume ratio) was used for the eluent for (rac-6); n-hexane/2-propanol/trifluoroacetic acid=90/10/0.1 (volume ratio) was used for (rac-7); n-hexane/2-propanol=60/40 (volume ratio) was used for (rac-8); and the eluent flow rate was 1.0 mL/min in all instances. The resulting chromatograms were used to calculate the retention factor $k'_1$ for the raffinate component and the separation factor α. The results are given in Table 2.

C 4

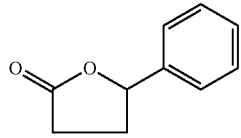
(ra-6)

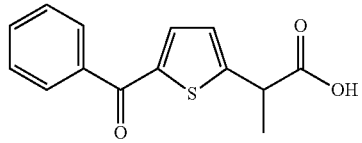
(ra-7)

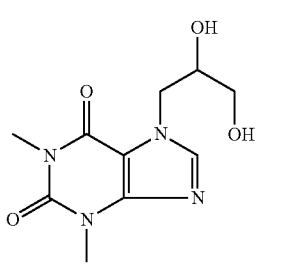

(ra-8)

TABLE 2

|  | Example 1 | | Comparative Example 1 | |
| --- | --- | --- | --- | --- |
| racemic body | $k'_1$ | α | $k'_1$ | α |
| γ-phenyl-γ-butyrolactone | 5.62 | 1.15 | 3.01 | 1.05 |
| tiaprofenic acid | 7.47 | 1.14 | 2.95 | 1.00 |
| diprophylline | 7.72 | 1.32 | 4.32 | 1.21 |

Comparative Example 1

A polysaccharide derivative was synthesized as in Example 1, but lowering the amount of 3-chloro-4-methylphenyl isocyanate used, which resulted in the synthesis of an amylose tris(3-chloro-4-methylphenylcarbamate) in which the average introduction ratio R by the 3-chloro-4-methylphenyl group was 3.0. Operating as in Example 1, a separating agent for optical isomers C1 and a column C1 for optical isomer separation were obtained, but using 15 g for the amount of silica gel, and the optical separation performance was evaluated. The results of the optical resolutions are shown in Tables 1 and 2.

As is clear from Tables 1 and 2, the column 1 for optical isomer separation, which has the amylose derivative with the higher average introduction ratio for R, exhibits a higher optical separation performance for all of the various racemic bodies referenced above than the column C1 for optical isomer separation, and as a result can be expected to exhibit a higher separation factor for various optical isomers than the column C1 for optical isomer separation.

INDUSTRIAL APPLICABILITY

Because in the present invention the Formula (2) atomic group can be constituted by combining two or more functional groups that act on the optical isomers targeted for separation in an optical resolution, the appearance can be expected, versus the optical resolving power of the heretofore known Formula (1) atomic group or the "—X—R2" in Formula (2), of a novel optical resolving power or an additionally improved optical resolving power. Thus, the present invention is expected to provide additional improvements in productivity in the production of optical isomers and to support the establishment of production technologies for novel optical isomers.

While the invention has been described in detail and with reference to specific embodiments thereof, it will be apparent to one skilled in the art that various changes and modifications can be made therein without departing from the spirit and scope thereof.

This application claims the benefit of Japanese Patent Application No. 2010-139485, filed on Jun. 18, 2010, which is hereby incorporated by reference herein its entirety.

What is claimed is:

1. A separating agent for optical isomers that contains a polysaccharide derivative, wherein
the polysaccharide derivative is provided by replacing all or a portion of hydrogen atoms on hydroxyl groups present in a cellulose or an amylose with the atomic groups represented by Formulae (1) and (2) below, and a sum of the average introduction ratios per monosaccharide unit of R1 and R2 in Formulae (1) and (2) below is greater than 3.0 but not more than 5.0:

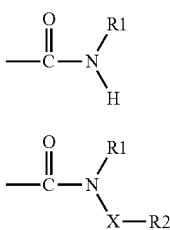

wherein, R1 and R2 each represent a $C_{1-18}$ monovalent aliphatic group which may have substituent selected from the group consisting of a $C_{1-18}$ alkyl group, an amino group, a halogen and a $C_{1-18}$ alkoxyl group or a $C_{6-18}$ monovalent aromatic group which may have substituent selected from the group consisting of a $C_{1-18}$ alkyl group, an amino group, a halogen and a $C_{1-18}$ akoxyl group and X represents an amide bond.

2. The separating agent for optical isomers according to claim 1, wherein R1 and R2 are the same.

3. The separating agent for optical isomers according to claim 1, wherein the polysaccharide derivative is derived from cellulose.

4. The separating agent for optical isomers according to claim 1, wherein the polysaccharide derivative is derived from amylose.

5. The separating agent for optical isomers according to claim 4, wherein the sum of the average introduction ratios is 3.2 and wherein R1 and R2 are a 3-chloro-4-methylphenyl group.

* * * * *